United States Patent [19]

Stegmann et al.

[11] Patent Number: 5,110,978
[45] Date of Patent: * May 5, 1992

[54] PROCESS FOR THE PREPARATION OF PHENOLIC THIOCARBOXYLIC ACID ESTERS

[75] Inventors: Werner Stegmann, Liestal; Reto Luisoli, Hölstein, both of Switzerland

[73] Assignee: Ciba-Geigy Corporation, Ardsley, N.Y.

[*] Notice: The portion of the term of this patent subsequent to Nov. 18, 2003 has been disclaimed.

[21] Appl. No.: 632,585

[22] Filed: Dec. 21, 1990

Related U.S. Application Data

[63] Continuation of Ser. No. 554,953, Jul. 17, 1990, abandoned, which is a continuation of Ser. No. 283,102, Dec. 12, 1988, abandoned.

[30] Foreign Application Priority Data

Dec. 22, 1987 [CH] Switzerland ............ 4987/87

[51] Int. Cl.⁵ ............................................. C07C 319/12
[52] U.S. Cl. ..................................... 560/15; 562/426; 568/51
[58] Field of Search ........................ 560/15; 562/426

[56] References Cited

U.S. PATENT DOCUMENTS 3,553,270  1/1971  Wollensak et al. ............... 568/46
3,832,328  8/1974  Eggensperger et al. ........... 524/289
4,623,745  11/1986  Rosenberger et al. ............. 560/15

Primary Examiner—Jose G. Dees
Assistant Examiner—Vera C. Clarke
Attorney, Agent, or Firm—Luther A. R. Hall

[57] ABSTRACT

A process for the preparation of compounds of formula I

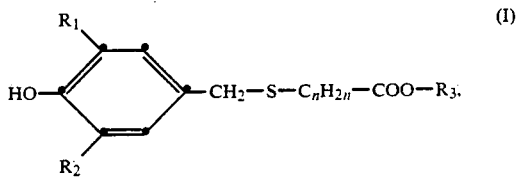

by reacting a phenol with formaldehyde and a thiol of formula $HS-C_nH_{2n}-COO-R_3$ under excess pressure and in the presence of dimethylamine.

The symbols $R_1$ and $R_2$ are independently alkyl, $R_3$ is alkyl or alkyl interrupted by —O— or —S—, and n is 1 or 2.

10 Claims, No Drawings

PROCESS FOR THE PREPARATION OF PHENOLIC THIOCARBOXYLIC ACID ESTERS

This application is a continuation of application Ser. No. 554,953, filed Jul. 17, 1990, which is a continuation of Ser. No. 283,102, filed Dec. 12, 1988, both now abandoned.

The present invention relates to a novel single step process for the preparation of thiocarboxylic acid esters by reacting a phenol with formaldehyde and a thiol.

It is known to prepare phenolic thioesters in two steps, either via the Mannich base or by reacting appropriate phenols with a thioacid and formaldehyde and subsequently esterifying the acids so obtained. Such a process is disclosed, for example, in U.S. Pat. No. 3,832,328. However, such two-step processes are complicated.

A single step process for the preparation of phenolic thioethers by reacting the appropriate phenol with formaldehyde and a thiol in the presence of a strong base such as triethylamine or, in particular, an alkali metal hydroxide, as catalyst, is disclosed in U.S. Pat. No. 3,553,270. Attempts to prepare phenolic thioesters as well by this method have failed.

A single step process for the preparation of phenolic thioesters by reacting a phenol with formaldehyde and a thioester is disclosed in U.S. Pat. No. 4,623,745. In this publication, $C_2$–$C_{20}$dialkylamines, for example, are cited as catalysts. Specifically, dibutylamine is used as catalyst.

As phenolic thioesters are useful antioxidants, there still exists a need to provide an improved process for their preparation. It has now been found that phenolic thioesters are obtained in high yield and purity in conveniently short reaction times by carrying out the reaction in the presence of mono- or dimethylamine or mono- or diethylamine, preferably dimethylamine.

Accordingly, the present invention relates to a process for the preparation of compounds of formula I

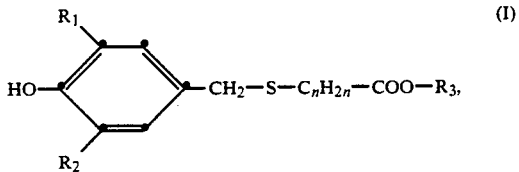

wherein $R_1$ and $R_2$ are each independently of the other $C_1$–$C_4$alkyl, $R_3$ is $C_1$–$C_{20}$alkyl or $C_2$–$C_{20}$alkyl which is interrupted by —O— or —S—, and n is 1 or 2, by reacting a phenol of formula II

with formaldehyde or a compound that releases formaldehyde under the reaction conditions, and with a thiol of formula III

$$HS-C_nH_{2n}-COO-R_3 \qquad (III)$$

wherein $R_1$, $R_2$, $R_3$ and n are as defined above, in the presence of a base, which process comprises carrying out the reaction under excess pressure and in the presence of mono- or dimethylamine or mono- or diethylamine as base.

$R_1$ and $R_2$ defined as $C_1$–$C_4$alkyl may be methyl, ethyl, n-propyl, isopropyl, n-butyl, sec-butyl or tert-butyl. Preferably $R_1$ is methyl and, most preferably, tert-butyl. $R_2$ is preferably tert-butyl.

$R_3$ defined as $C_1$–$C_{20}$alkyl is, in addition to the meaning of $R_1$, for example pentyl, hexyl, n-octyl, oct-3-yl, 2-ethyl-n-hexyl, 1,1,3,3-tetramethylbutyl, nonyl, decyl, dodecyl, tridecyl, hexadecyl, octadecyl or eicosyl. The preferred meaning of $R_3$ is 2-ethylhexyl, oct-3-yl or iso-tridecyl (mixture of tridecyl isomers).

Examples of $R_3$ defined as $C_2$–$C_{20}$alkyl which is interrupted by —O— or —S— are: methoxymethyl, 2-ethoxyethyl, 2-n-butoxyethyl, 3-n-butoxypropyl, 2-octoxyethyl, 2-hexadecyloxyethyl, 2-ethoxymethyl, butoxymethyl, methoxypropyl, ethoxypropyl, 3-thiaheptyl or 3-thia-5-methylhexyl. n is preferably 1.

Preferred compounds obtained by the process of this invention are those wherein $R_1$ and $R_2$ are each independently of the other methyl or tert-butyl and $R_3$ is $C_6$–$C_{14}$alkyl, and, most particularly, those wherein $R_1$ and $R_2$ are tert-butyl and n is 1.

Particularly preferred compounds obtained by the process of this invention are those wherein $R_1$ and $R_2$ are tert-butyl, n is 1 and $R_3$ is 2-ethylhexyl, oct-3-yl or isotridecyl.

In the process of this invention, the reactants, namely phenol, formaldehyde and a thiol, can be used in stoichiometric amounts. On occasion, however, it can be advantageous to use an excess of formaldehyde and/or thiol.

The process of this invention is carried out in the presence of mono- or dimethylamine or mono- or diethylamine as base. It is preferred to use mono- or dimethylamine, most particularly dimethylamine.

The base can be used in an amount of 1–50 mol %, preferably 10–25 mol %, based on the thiol.

It is particularly expedient to carry out the process of the invention under an excess pressure of $10^5$ to $10^6$ Pa. The reaction temperature is, for example, in the range from 80° to 200° C. A preferred temperature range is from 120° to 150° C.

The reaction times can vary, depending on the phenol and the thiol, and are, for example, from 30 minutes to 6 hours, preferably from 45 minutes to 4 hours.

The process of the invention can be carried out with or without a solvent. If a solvent is used, about 20% by weight will suffice, based on the final product. This amount constitutes a substantial reduction compared with the customary amounts of solvent and is an advantage of the process.

Suitable solvents are those in which the reactants are soluble to a certain degree and which are essentially inert under the reaction conditions. Examples of such solvents are hydrocarbons such as toluene, xylene, octane and β-terpene; ethers such as dioxan, diethyl ether, dimethyl ethers of ethylene glycol, tetrahydrofuran and the like. Chlorinated hydrocarbons such as carbon tetrachloride, chloroform, trichloroethane, and perchloroethylene can also be conveniently used as solvents. Primary and secondary alcohols of 3 to 6 carbon atoms, for example isopropanol, sec-butyl alcohol, tert-butyl alcohol, tert-amyl alcohol, and hexyl alcohol can also be recommended for successfully carrying out the process of the invention.

It is preferred, however, to carry out the process of the invention in the absence of a solvent.

Formaldehyde, or a compound that releases formaldehyde under the reaction conditions, for example paraformaldehyde or hexamethylenetetramine, is used in the process of the invention. It is preferred to use formaldehyde and, most particularly, paraformaldehyde.

After the reaction mixture has been cooled, the final product can be obtained, for example, by distillation and, if desired, purified.

It is, however, a further advantage of the process of the invention that the final products are obtained in a purity that permits their direct further use for many utilities. If it is nevertheless desired to purify the final products, then the distillation is preferably carried out in a flash distillation apparatus, preferably under a pressure of 0.5–5 Pa.

The starting phenols and thiols are known compounds and some are commercially available or can be prepared by known methods.

The compounds of formula I prepared by the process of this invention are known compounds and can be used as stabilizers for protecting organic material against degradation caused by the action of oxygen, heat, light or energy-rich radiation.

The preferred utility of the compounds is as antioxidants in organic polymers and in elastomers, or in mineral oils or synthetic lubricants as disclosed, for example, in EP-A 0 059 168.

The invention is illustrated in more detail by the following Examples, in which parts and percentages are by weight, unless otherwise stated.

EXAMPLE 1

Preparation of 2'-ethylhexyl 3,5-di-tert-butyl-4-hydroxybenzylthioglycolate

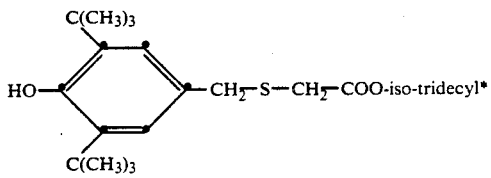

An apparatus consisting of a 750 ml reactor (approved up to 3·10 Pa) which is equipped with stirrer, thermometer, nitrogen supply and gas inlet pipe, as well as with distillation head with condenser and receiver with vacuum connection, is charged in succession with 206.3 g (1.0 mol) of 2,6-di-tert-butylphenol, 36.0 g (1.2 mol) of 100% paraformaldehyde and 204.0 g (1.0 mol) of 2-ethylhexylthioglycolate. The suspension is blanketed with nitrogen and then, with moderate stirring, evacuated to 2000 Pa and the reactor is closed. Then 4.5 g (0.1 mol) of gaseous dimethylamine are passed into the suspension through the gas inlet pipe over 10 minutes, whereupon the reaction mixture exotherms slightly and the temperature rises by ca. 5° C. and the vacuum in the reaction vessel is ca. 1.2·10⁴ Pa.

The pale, mobile suspension is heated to 130° C. and stirred for 4–5 hours at this temperature, the pressure rising to 2.5·10⁵ Pa. The suspension becomes a clear, orange-yellow melt which, towards the end of the reaction, becomes highly turbid owing to the water of reaction. The reaction mixture is cooled to 70° C. and, at this temperature, a mixture of dimethylamine, water and some excess formaldehyde is removed by distillation by applying a vacuum of 2000 Pa, until at 100° C. and 2000 Pa the distillation is complete.

Yield: 413.5 g (98% of theory) of the final product with a refractive index $n_D^{20} = 1.5140$.

EXAMPLE 2

The procedure of Example 1 is repeated, using 146.0 g (2.0 mol) of dimethyl formamide as solvent. The suspension is stirred for 45 minutes at 125° C., the pressure rising from ca. 1.2·10⁴ to 1.5·10⁵ Pa.

Yield: 435 g (99% of theory) of the desired final product with a refractive index $n_D^{20} = 1.5120$.

EXAMPLE 3

Preparation of isotridecyl 3,5-di-tert-butyl-4-hydroxybenzylthioglycolate

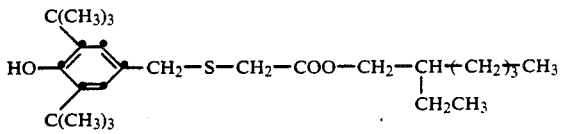

*mixture of tridecanol isomers

An apparatus as described in Example 1 is charged at room temperature, in succession, with 164.8 g (0.8 mol) of 2,6-di-tert-butylphenol, 219.6 g (0.8 mol) of isotridecyl thioglycolate and 26.4 g (0.88 mol) of 100% paraformaldehyde.

The suspension is blanketed with nitrogen and then evacuated to 2000 Pa with moderate stirring, and the reactor is closed. Then 9.3 g (0.206 mol) of gaseous dimethylamine are passed into the suspension through the gas inlet pipe over 10 minutes. The ensuing reaction is markedly exothermic. The temperature rises by ca. 5°–10° C. and the vacuum in the reactor is ca. 2.5·10⁴ Pa.

The pale, mobile suspension is heated to 140° C. and stirred for 4–5 hours at this temperature, the pressure rising to 2.3·10⁵. The suspension becomes a clear, yellowish-brown melt which, towards the end of the reaction, becomes highly turbid owing to the water of reaction. The reaction mixture is cooled to 70° C. and, at this temperature, 10.0 g of fluid cracking catalyst (CFC) as absorber are added and, by applying a vacuum of 2000 Pa, a mixture of dimethylamine, water and some excess paraformaldehyde is distilled off until, at 100° C., the distillation is complete. The melt is thereafter freed from absorber by clarifying filtration at 100° C.

Yield: 375 g (95% of theory) of the final product with a refractive index $n_D^{20} = 1.5063$.

EXAMPLE 4

The procedure of Example 3 is repeated, using 114.0 g (1.56 mol) of dimethyl formamide as solvent and 5.7 g (0.126 mol) of dimethylamine. The suspension is stirred at 130°–140° C. for 1.5 hours, the pressure rising to 1.9·10⁵ Pa.

Yield: 367 g (93% of theory) of the final product with a refractive index $n_D^{20} = 1.5080$.

EXAMPLE 5

Preparation of oct-3-yl 3,5-di-tert-butyl-4-hydroxybenzylthioglycolate

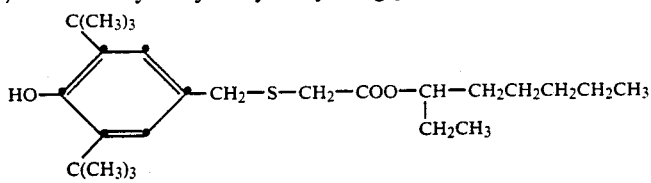

The procedure of Example 3 is repeated, using 247.6 g (1.20 mol) of 2,6-di-tert-butylphenol, 244.8 g (1.20 mol) of oct-3-yl thioglycolate, 39.6 g (1.32 mol) of 100% paraformaldehyde and 18.0 g (0.40 mol) of dimethylamine. The suspension is stirred for 4 hours at 125° C., the pressure rising to $2.3 \cdot 10^5$ Pa.

Yield: 482 g (95% of theory) of the final product as a yellow fluid with a refractive index $n_D^{20}=1.5130$.

EXAMPLE 6

Purification by Flash Distillation

The crude product of each of Examples 1–5 is fed at a rate of 450 g per hour into a flash distillation apparatus (glass 0.04 m²) at a jacket temperature of 160° C. a condenser temperature of 27° C., a wiper speed of 250 rpm and a pressure of 0.5 Pa.

Each distillation affords a clear, pale yellow to yellow product in a yield of ca. 93%, based on the amount of crude product.

EXAMPLE 7

Preparation of 3',4'-dimethylhex-1'-yl 3,5-di-tert-butyl-4-hydroxybenzylthioglycolate

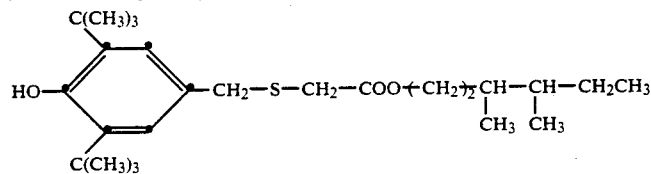

The procedure of Example 1 is repeated, using 247.6 g (1.2 mol) of 2,6-di-tert-butylphenol, 244.8 g (1.2 mol) of isooctyl thioglycolate (mixture of isomers), 39.6 g (1.32 mol) of paraformaldehyde and 18.0 g (0.4 mol) of dimethylamine. A reaction course identical to that of Example 1 is observed. The pressure rises during the reaction to $2.3 \cdot 10^5$ Pa.

Yield: 472 g (93% of theory) of the final product with a refractive index $n_D^{20}=1.5145$.

This product can be readily further purified by distillation in a thin-film evaporator (head temperature: 240° C. at 5 mbar), to give the final product in a purity of over 97%. The density is 1.0043 g/ml at a viscosity (at 40° C.) of 197–198 mPa·s.

What is claimed is:

1. A process for the preparation of a compound of formula I

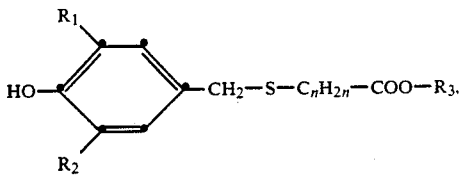

wherein $R_1$ and $R_2$ are each independently of the other $C_1$–$C_4$alkyl, $R_3$ is $C_1$–$C_{20}$alkyl or $C_2$–$C_{20}$alkyl which is interrupted by —O— or —S—, and n is 1 or 2, by reacting a phenol of formula II

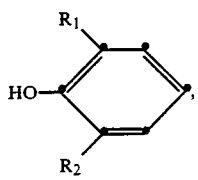

with formaldehyde or a compound that releases formaldehyde under the reaction conditions, and with a thiol of formula III

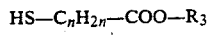

$$HS-C_nH_{2n}-COO-R_3 \qquad (III)$$

wherein $R_1$, $R_2$, $R_3$ and n are as defined above, in the presence of a base, which process comprises carrying out the reaction under excess pressure and in the presence of mono- or dimethylamine or mono- or diethylamine as base.

2. A process according to claim 1, wherein 1–50 mol % of the base is used, based on the thiol.

3. A process according to claim 1, wherein the reaction is carried out in the absence of a solvent.

4. A process according to claim 1, wherein an excess pressure of $10^5$ to $10^6$ Pa is applied.

5. A process according to claim 1, wherein the reaction temperature is in the range from 120° to 150° C.

6. A process according to claim 1, wherein the crude product of formula I is purified by flash distillation.

7. A process according to claim 1 for the preparation of a compound of formula I, wherein $R_1$ and $R_2$ are each independently of the other methyl or tert-butyl and $R_3$ is $C_6$–$C_{14}$alkyl.

8. A process according to claim 7 for the preparation of a compound of formula I, wherein $R_1$ and $R_2$ are tert-butyl and n is 1.

9. A process according to claim 8 for the preparation of a compound of formula I, wherein $R_3$ is 2-ethylhexyl, oct-3-yl or isotridecyl.

10. A process according to claim 1, wherein the base is dimethylamine.

* * * * *